United States Patent [19]
Alter

[11] Patent Number: 5,580,724
[45] Date of Patent: Dec. 3, 1996

[54] DIFFERENTIAL EXPANSION OF FETAL STEM CELLS IN MATERNAL CIRCULATION FOR USE IN PRENATAL GENETIC ANALYSIS

[75] Inventor: Blanche P. Alter, Galveston, Tex.

[73] Assignee: Board of Regents, The University of Texas System, Austin, Tex.

[21] Appl. No.: 218,290

[22] Filed: Mar. 25, 1994

[51] Int. Cl.$^6$ .............................. C12Q 1/68; C12N 5/06; C12N 5/08
[52] U.S. Cl. .............................. 435/6; 435/240.2; 435/4; 935/76; 935/77; 935/78
[58] Field of Search .............................. 435/6, 5, 240.2, 435/7.21, 7.24, 7.25; 436/63, 94, 518; 935/76, 77, 78

[56] References Cited

FOREIGN PATENT DOCUMENTS

| | | |
|---|---|---|
| 9116452 | 10/1991 | WIPO . |
| 9308269 | 4/1993 | WIPO . |
| WO93/08268 | 4/1993 | WIPO . |
| WO93/18136 | 9/1993 | WIPO . |
| WO94/16715 | 8/1994 | WIPO . |

OTHER PUBLICATIONS

Brugger et al Blood (1993) 81:2579.2584.
Lee, "The Role of Interleukin-6 in Development," *Developmental Biology*, 151:331–338, 1992.
Y-M Lo et al., "Culture of Fetal Erythroid Cells from Maternal Peripheral Blood," *The Lancet*, 344:264, Jul. 1994.
Mueller et al., "Isolation of Fetal Trophoblast Cells form Peripheral Blood of Pregnant Women," *The Lancet*, 336:197–200, 1990.
Pool et al., "Trophoblast Cells and Maternal Blood," *The Lancet*, 804–805, Apr. 1987.
PCT Search Report, PCT/US95/03659, Jul. 24, 1995.
Bianchi et al., 1993, "Erythroid–specific antibodies enhance detection of fetal nucleated erythrocytes in maternal blood," *Prenat. Diagn.* 13:293–300.
Fibach et al., 1989, "Proliferation and maturation of human erythroid progenitors in liquid culture," *Blood*, 73:100–03.
Forestier, et al., 1991, "Developmental hematopoiesis in normal human fetal blood," *Blood*, 77:2360–63.
McNiece et al., 1991, "Recombinant human stem cell factor synergizes with GM–CSF, G–CSF, IL–3 and Epo to stimulate human progenitor cells of the myeloid and erythroid lineages," *Exp. Hematol.*, 19:226–31.
Gardner et al., 1990, "Effects of interleukin–6 on fetal hematopoietic progenitors," *Blood*, 75:2150–55.
Parks et al., 1982, "Fetal cells from maternal blood: Their selection and prospects for use in prenatal diagnosis," *Methods in Cell Biology*, 26:277–95.
Weinberg et al., 1992, "Erythropoiesis is distinct at each stage of ontogeny," *Pediatr. Res.*, 31:170–75.
Weinberg et al., 1993, "Stem cell factor amplifies newborn and sickle erythropoiesis in liquid cultures," *Blood*, 81:2591–99.
Houston Chronicle advertisement, Feb. 19, 1994.

*Primary Examiner*—Stephanie W. Zitomer
*Assistant Examiner*—Carla Myers
*Attorney, Agent, or Firm*—Arnold, White & Durkee

[57] ABSTRACT

The methods of the present invention use blood of pregnant females and fetal cell amplification to facilitate prenatal diagnosis without invading fetal space. This method is less invasive and simpler than amniocentesis or chorionic villus sampling because it involves only drawing blood from the mother to obtain a fetal cell sample. If there is a specific disease with known molecular mutations being sought, cells from the sample are a source of DNA enriched for fetal material. If the disease is one involving red cells, this method provides fetal red cells for analysis. If the disease involves white cells, different cytokines can be used to selectively produce fetal leukocytes. When an abnormal chromosome pattern without a specific diagnostic risk (e.g., advanced maternal age) is being sought, then the culture method provides dividing cells of fetal origin.

7 Claims, 11 Drawing Sheets

PROGENITORS:   STEM CELL ⟶ BFU-E ⟶ CFU-E

PRECURSORS:    PRO- ⟶ BASOPHILIC

POLYCHROMATOPHILIC ⟶ ORTHOCHROMATIC

ERYTHROBLASTS

PROGENY:       RETICULOCYTE ⟶ ERYTHROCYTE

FIG.1

DIFFERENTIAL EXPANSION OF FETAL STEM CELLS IN MATERNAL CIRCULATION FOR USE IN PRENATAL GENETIC ANALYSIS

BACKGROUND OF THE INVENTION

The present invention relates to noninvasive sampling of fetal cells for the purpose of prenatal diagnosis of genetic diseases. Candidate cells proposed by others include leukocytes, erythroid cells, and trophoblasts. Estimates of the amount of fetal blood which crosses into the maternal circulation in the first or second trimester include 2 µL per day or a total of 50 to 200 µL by the midtrimester (Parks et al.). Other estimates suggest that about 1/50,000 cells are fetal (Schroder et al. ). A recent study determined that this ratio increased from 1/144,000 at 15 weeks gestation to 1/4,000 later in pregnancy (Hamada et al.).

Abbreviations used herein include:

| | |
|---|---|
| BFU-E | Burst forming unit-erythroid |
| BPA | Burst promoting activities |
| BSA | Bovine serum albumin |
| CFU-E | Colony forming unit-erythroid |
| Ep | Erythropoietin |
| FACS | Fluorescence-activated cell sorting |
| FCS | Fetal calf serum |
| FISH | Fluorescence in situ hybridization |
| GM-CSF | Granulocyte-macrophage colony stimulating factor |
| GPA | Glycophorin A |
| Hb | Hemoglobin |
| IL-3 | Interleukin-3 |
| IL-6 | Interleukin-6 |
| MACS | Magnetic-activated cell sorting |
| MNC | Mononuclear cells |
| MRNA | Messenger ribonucleic acid |
| PCR | Polymerase chain reaction |
| RT-PCR | Reverse transcription PCR |
| SCF | Stem cell factor |
| TFR | Transferrin receptor |
| TSPR | Thrombospondin receptor |

Zipursky et al. were the first to demonstrate fetal red cells in maternal blood (albeit, immediately following delivery), using the Kleihauer-Betke stain for fetal hemoglobin (Zipursky et al.). Schröder reviewed this topic in 1975 and suggested that more than 1 fetal cell per 50,000 maternal cells was present in 5–10% of pregnancies in the second trimester (SchröSder et al.). Parks and Herzenberg used fluorescence activated cell sorting (FACS) and found Rh D$^+$ red cells in the blood of all Rh D$^-$ ABO compatible mothers in frequencies ranging from 1:4,000 to 1:80,000, corresponding to 200 µL of fetal blood (Parks et al.). Fetal erythroblasts (and reticulocytes) in maternal blood were identified as early as 16 weeks gestation using fluorescence activated cell sorting (FACS) with monoclonal antibodies to the transferrin receptor (TFR) by Bianchi et al. (1990) Price et al. enhanced the enrichment with the addition of antibody to glycophorin A (GPA), and sorting according to cell size (forward angle light scatter) and granularity (side scatter). They concluded that there was an enrichment from 1 fetal nucleated red cell per $10^7$ maternal cells to 1 per 10–20 cells, using in situ hybridization with markers for X and Y chromosomes. Gänshirt-Ahlert et al. suggested that magnetic-activated cell sorting (MACS) with microbeads would be faster than FACS, but found that antibody to TFR was not efficient for the enrichment of nucleated fetal cells, since many erythroblasts were non-reactive, and many reticulocytes (fetal and maternal) were TFR-positive. Bianchi et al. (1993) then combined antibodies to TFR, GPA, and to the thrombospondin receptor (TSPR), and found that GPA was the most important marker for recovery of fetal nucleated cells. Many of the analyses using TFR and GPA did not determine the final proportion of fetal/maternal cells; they used either polymerase chain reaction (PCR) amplification of DNA for Southern blots or fluorescence in situ hybridization (FISH) to detect male cells or fetal aneuploidy.

The presence of fetal white cells in the pregnant mother's blood was suggested as early as 1969 by Walknowska et al., based on the detection of XY karyotype in 0.2 to 1% of lymphocytes. In similar studies, examining for Y chromosomes or Y fluorescence in interphase cells, fetal lymphocytes comprised about 0.1 to 1% (Schroder et al., 1972; De Grouchy et al.; Schroder et al., 1975; Grosset, et al.; Siebers et al.; and Kirsch-Voiders et al.). Herzenberg et al. used FACS to sort for paternal HLA types, and found Y-positive cells at an incidence of 3 per 1,000 sorted cells; a larger study by the same group found an incidence of 1/800 to 1/60,000 (Iverson et al.). One group stained maternal mononuclear cells (MNC) for α-fetoprotein and found 1/1,000 positive cells (Kulozik et al.). Nakagome et al. used PCR amplification of Y DNA from unseparated maternal cells and found no positives, indicating that fetal cells were less than 1/25,000 maternal cells. However, Kao et al. were able to correctly identify male fetuses with this approach and indicated that 2 fetal cells were sufficient. Lo et al. used nested PCR with 2 sets of Y-specific primers, and could find 1 male in 300,000 female cells. To circumvent the possibility of residual lymphocytes from earlier male pregnancies, Wessman et al. used anti-My7 to identify granulocytes on cytospin slides of maternal mononuclear cells and found that about 0.1% were Y$^+$ using in situ hybridization. Thus, the sensitivity of detection of fetal leukocytes in maternal blood varies widely, perhaps dependent on the assay method, the method of enrichment, and the gestational age; the specificity also varies, with most reports including false negatives as well as false positives.

Another cell type which was sought is trophoblasts, which might be distinguished with the monoclonal antibody H315 (Covone et al., 1984, and Mueller et al.). However, H315-positive cells were found in nonpregnant women (Pool et al. ), and the consensus is that nontrophoblast cells may absorb this antigen (Covone et al. 1988). Indeed, Bruch et al. reported that positive cells sorted with 3 monoclonal antibodies to trophoblasts had the morphology of leukocytes. Cacheux et al. depleted maternal lymphocytes with monoclonal antibodies and magnetic beads, and then used trophoblast antibodies and FACS; 4% of 1,000 recovered cells were Y-positive by FISH.

The major methods for cell separation have included labelling with monoclonal antibodies, and separating with FACS, with Dynal magnetic beads, or micromagnetic beads (MACS). After separation, the resulting semipurified cells are then examined using PCR amplification or in situ hybridization of specific genes or chromosomes or by standard karyotyping of metaphases.

SUMMARY OF THE INVENTION

The methods of the present invention use blood of pregnant females and fetal cell amplification to facilitate prenatal diagnosis without invading fetal space. This method is less invasive and simpler than amniocentesis or chorionic villus sampling because it involves only drawing blood from the mother to obtain a fetal cell sample. If there is a specific disease with known molecular mutations being sought, cells from the sample are a source of DNA enriched for fetal material. If the disease is one involving red cells, this method provides fetal red cells for analysis. If the disease involves white cells, different cytokines can be used to selectively produce fetal leukocytes. When an abnormal chromosome pattern without a specific diagnostic risk (e.g., advanced maternal age) is being sought, then the culture method provides dividing cells of fetal origin.

Although the aim may be as simple as fetal sex determination, some difficulties may arise in optimally effective usage of the present invention. DNA analyses are most readily done when molecular markers are available, as is known in current technology. There may be insufficient leakage of fetal stem cells into the maternal circulation. The fetus may have an intrinsic hematopoietic disease which results in decreased numbers of stem cells in the circulation. The mother may have a hematologic disease such as sickle cell disease whereby her own stem cells are expanded and the selective growth advantage of the fetal stem cells is obscured.

BRIEF DESCRIPTION OF THE DRAWINGS

FIG. 1 is a scheme of erythropoiesis; progenitors are defined by in vitro assays while precursors and progeny are morphologically identifiable in bone marrow and blood.

FIG. 3A, fetal. FIG. 3B, newborn. FIG. 3C, adult. (Weinberg et al. 1992).

FIG. 4A and FIG. 4C are data from day 13; FIG. 4B and FIG. 4D are data from the day of peak growth. In FIG. 4A and FIG. 4B, data are expressed as colonies/100,000 cells plated. In FIG. 4C and FIG. 4D, data are expressed as BFU-E/mL of blood. Open symbols represent individual experiments; solid symbols represent the mean ±1 SD. (Weinberg et al. 1992).

FIG. 5A, Day 0 mononuclear cells before culture. FIG. 5B, Cells recovered from the first phase of culture after 7 days. FIG. 5C, hemoglobinized erythroblasts appear after 7 days in the second phase with Ep. FIG. 5D, Mature erythroblasts and erythrocytes recovered after 14 days in the second phase with Ep. From Weinberg et al. 1993.

DETAILED DESCRIPTION OF THE PREFERRED EMBODIMENTS

The present invention concern a new approach to enrich for fetal hematopoietic progenitor cells. Several studies indicate that fetal progenitors differ from those of adults (Weinberg et al. 1992; Forestier et al.). Cultures of mononuclear cells obtained from maternal blood are used to improve the proportion of fetal to adult progeny by manipulation of culture conditions. The inventor's previous studies indicate that there may be advantageous differences between fetal, newborn, and adult erythroid progenitor cells. The presence of fetal stem cells in maternal blood is an important aspect of the present invention.

Genetics Institute, Inc., 87 Cambridge Park Drive, Cambridge Mass. 02140 supplied IL-6. Amgen, Inc., Amgen Center, 1840 Dehavilland Drive, Thousand Oaks, Calif. 91320-1789 supplied SCF. Immunex, 51 University Street, Seattle Wash. 98101, supplied IL-3.

Figure 2A:
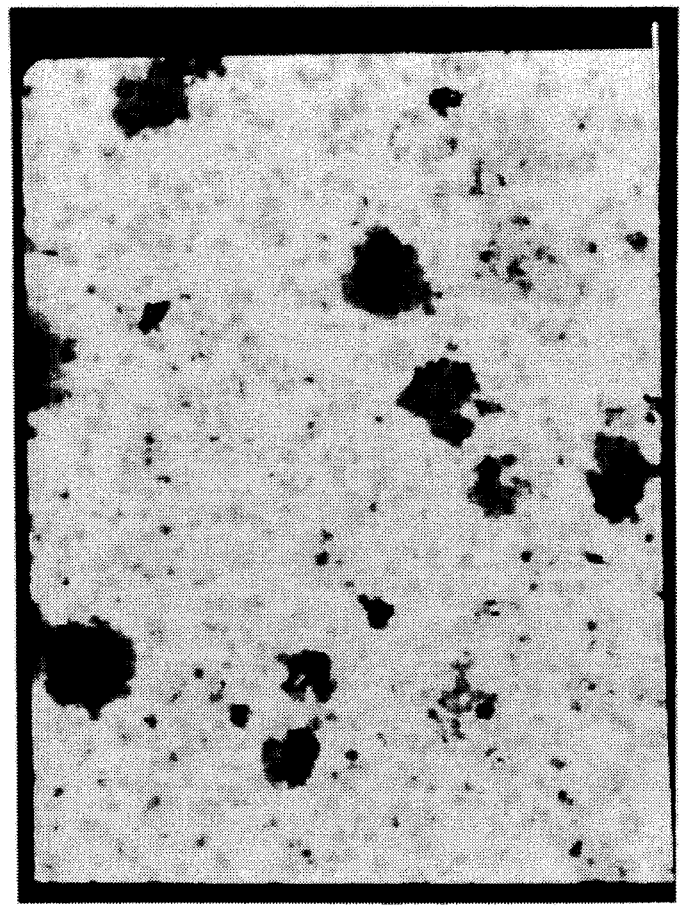
FIG. 2A shows colonies derived from CFU-E.
Figure 2B:
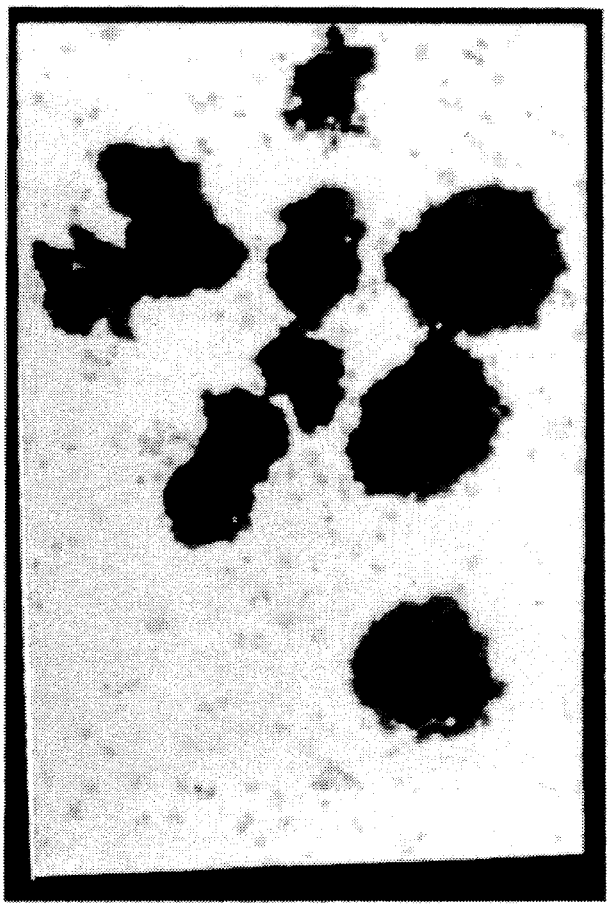
FIG. 2B shows a burst derived from one BFU-E.

The pluripotent stem cell, when present in the circulation at all, is in such a low proportion that finding this fetal component in the adult is quite difficult. The term "progenitor" is used for cells which are committed to a specific lineage, and are not morphologically recognizable, but are identified by their progeny (FIG. 1). The earliest erythroid cell is called the BFU-E (burst forming unit-erythroid) (Axelrad). Blood or bone marrow mononuclear cells are isolated by recovering the light density fraction after centrifugation on Ficoll-hypaque, and cultured in methyl cellulose or plasma clot, with erythropoietin (Ep), plus fetal calf serum, or defined serum-free media which include burst promoting activities (BPA), such as interleukin-3 (IL-3) or granulocyte-macrophage colony stimulating factor (GMCSF). The method currently used is described in detail by Weinberg et al. (1983). After about 14 days, a large colony with several subcolonies of hemoglobinized erythroblasts can be easily identified. A more mature progenitor, the CFU-E (colony forming unit-erythroid) requires Ep, and develops within 7–8 days into a small colony containing 8–132 erythroblasts (FIG. 2). "Precursors" are more mature than progenitors, and are morphologically identifiable without culture. In the erythroid series these include proerythroblasts, basophilic, polychromatophilic, and orthochromatic erythroblasts. These then enucleate and thus no longer contain DNA. However, the reticulocytes do contain globin RNA, and may be used for the diagnosis of hemoglobinopathies.

Table 1 outlines some specific markers (usually surface antigens) for the various stages of erythropoiesis (Sieff et al.; Loken et al.; Okumura et al.; Papayannopoulou et al.)

TABLE I

| Marker | Markers of Erythroid Differentiation | | | | | |
|---|---|---|---|---|---|---|
| | Stem | BFU-E | CFU-E | Eblast | Retic | RBC |
| CD34 | ++ | ++ | | | | |
| CD33 | | ++ | | | | |
| 17F11 (kit) | + | ++ | | | | |
| DR (activation) | | ++ | +? | | | |
| CD71 (TFR) | | +? | + | ++ | + | |
| CD36 (TSPR) | | | +? | ++ | ++ | + |
| Blood group A | | | | + | ++ | ++ |
| GPA | | | | + | ++ | ++ |
| Hb RNA | | | | ++ | + | |
| Hb protein | | | | + | ++ | +++ |

The markers are surface membrane antigens. Kit = c-kit. TFR - transferrin receptor. TSPR = thrombospondin receptor. GPA = glycophorin A. Hb = hemoglobin.

These antigens do not usually distinguish fetal from adult cells, and thus using monoclonal antibodies directed against those antigens with maternal mononuclear cells serves to define only a specific category; if the fetal contribution to that compartment is in relative excess (e.g., erythroblasts), then a partial selection for fetal cells can be achieved. CD34 identifies the earliest stem and progenitor cells, but is lost as the progenitors mature. CD33 appears after the stem cell stage, but disappears by the level of the CFU-E. The c-kit tyrosine kinase receptor is present early, and also decreases after BFU-E. Markers which appear in late BFU-E, characterize CFU-E and erythroblasts and persist on reticulocytes, include the transferrin receptor and the thrombospondin receptor. Markers of differentiated erythropoiesis are blood group antigens, glycophorin A, globin RNA, and globin protein.

Figure 3A:
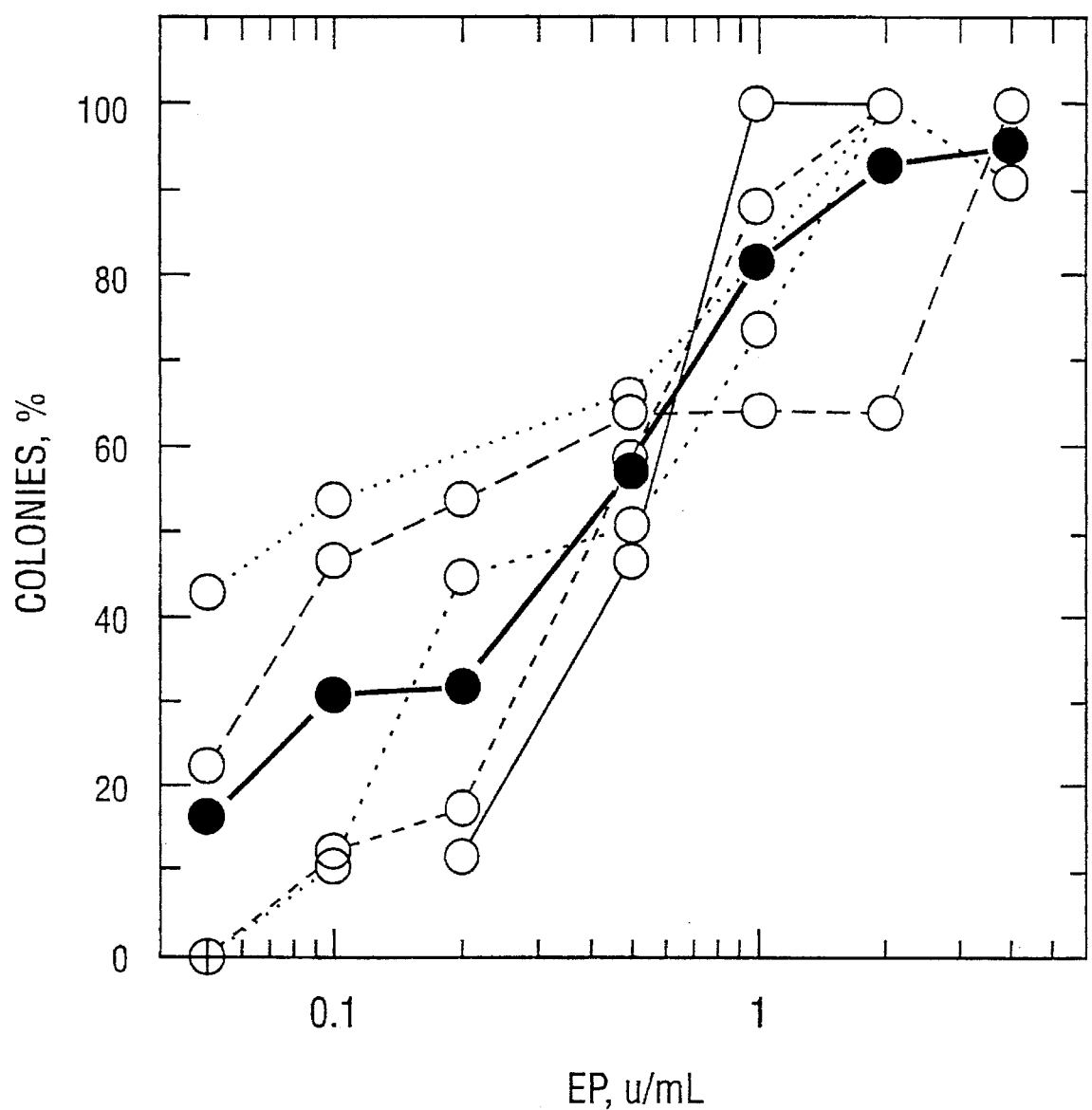
FIGS. 3A–3C show erythropoietin dose-response curves of blood BFU-E-derived colonies from fetuses, newborn infants, and adults. Data were normalized as the percentage of maximal growth. Each curve with open symbols represents a different donor, and each point is the mean of triplicate cultures. The curve with solid symbols represents the mean of all curves.
Figure 3B:
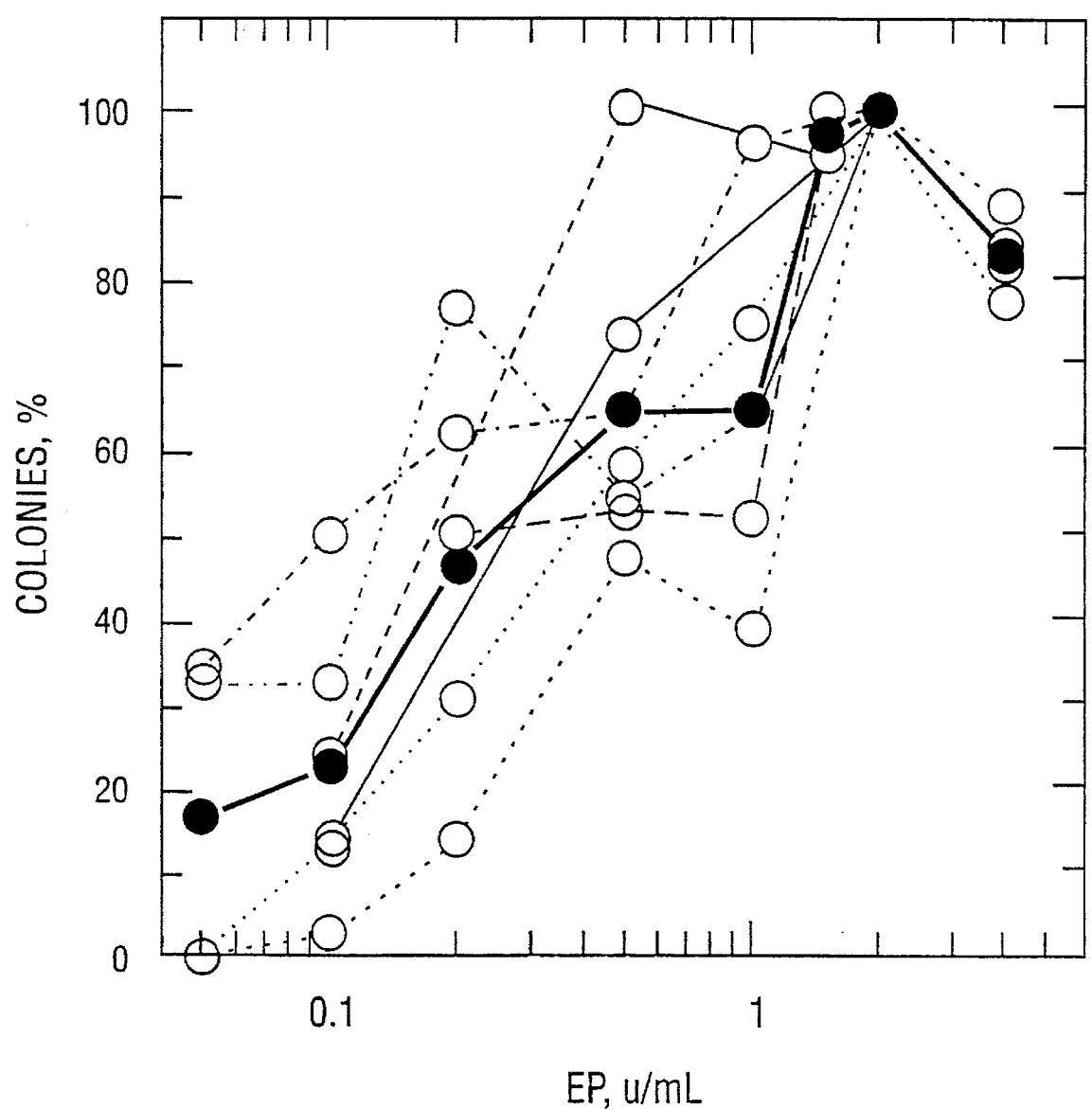
Figure 3C:
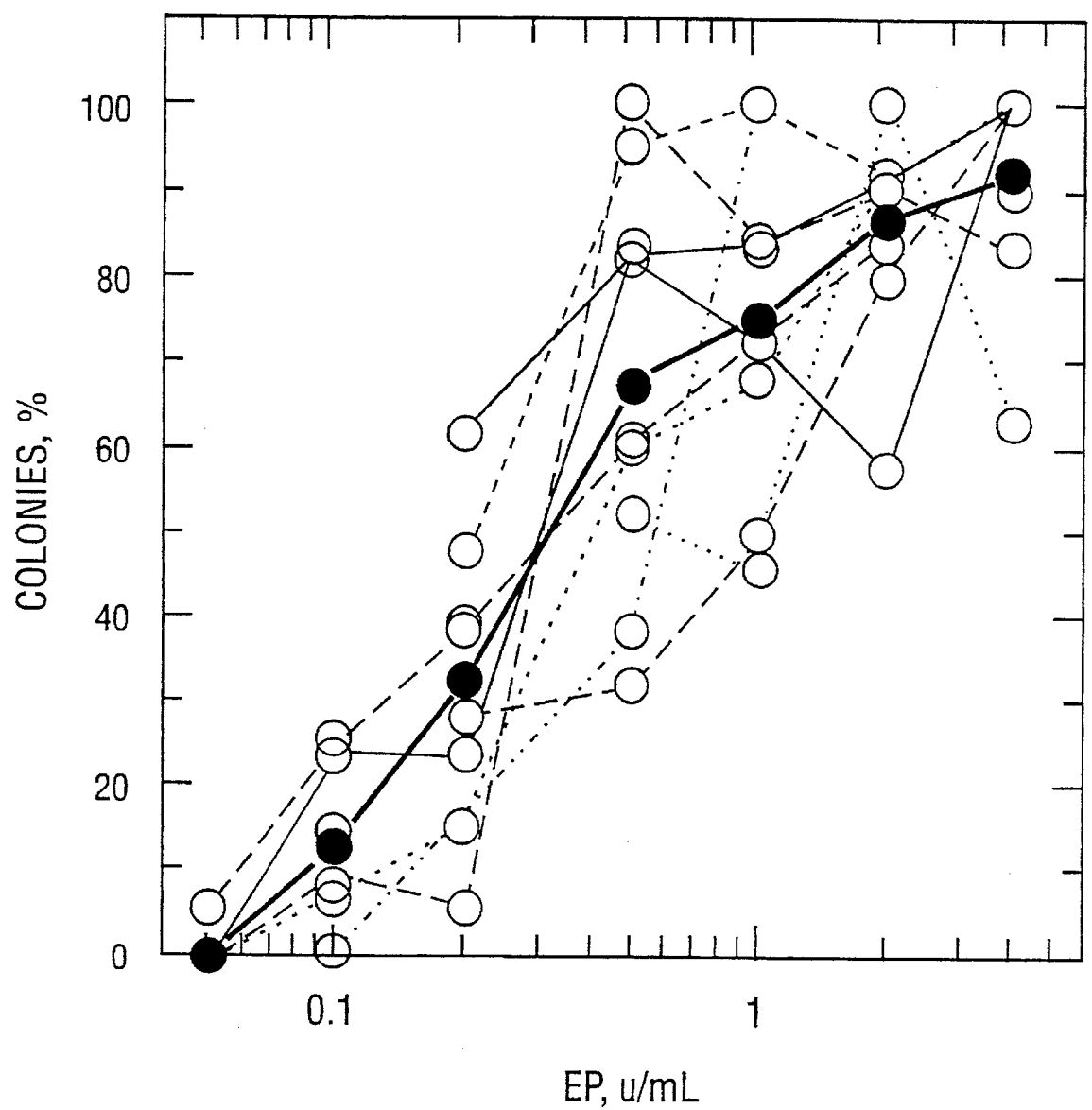
Figure 4A:
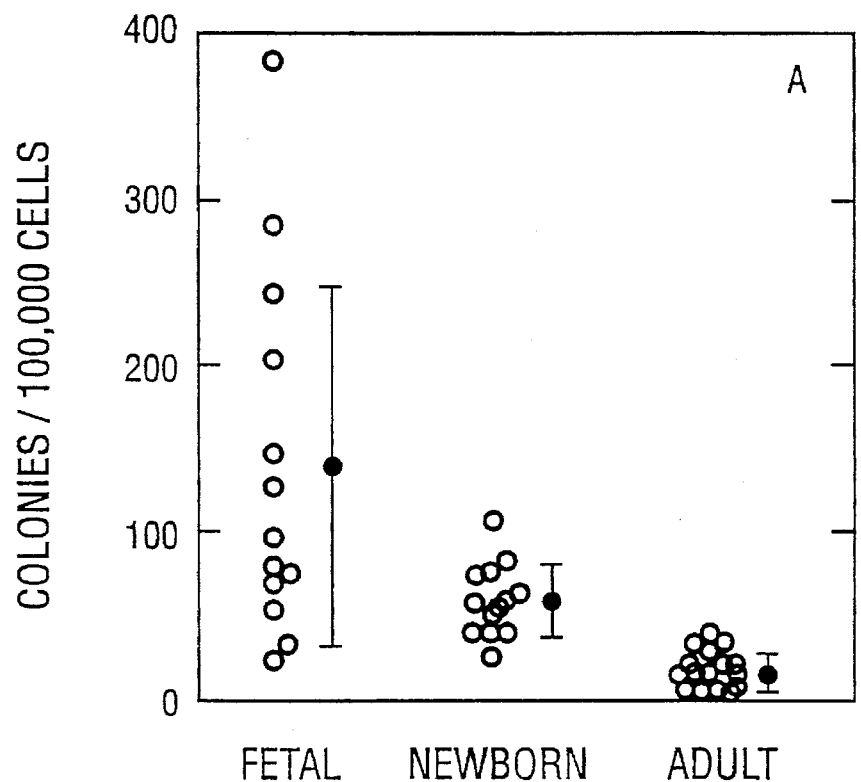
FIGS. 4A–4D show growth potential of blood erythroid progenitors from fetuses, newborn infants and adults.
Figure 4C:
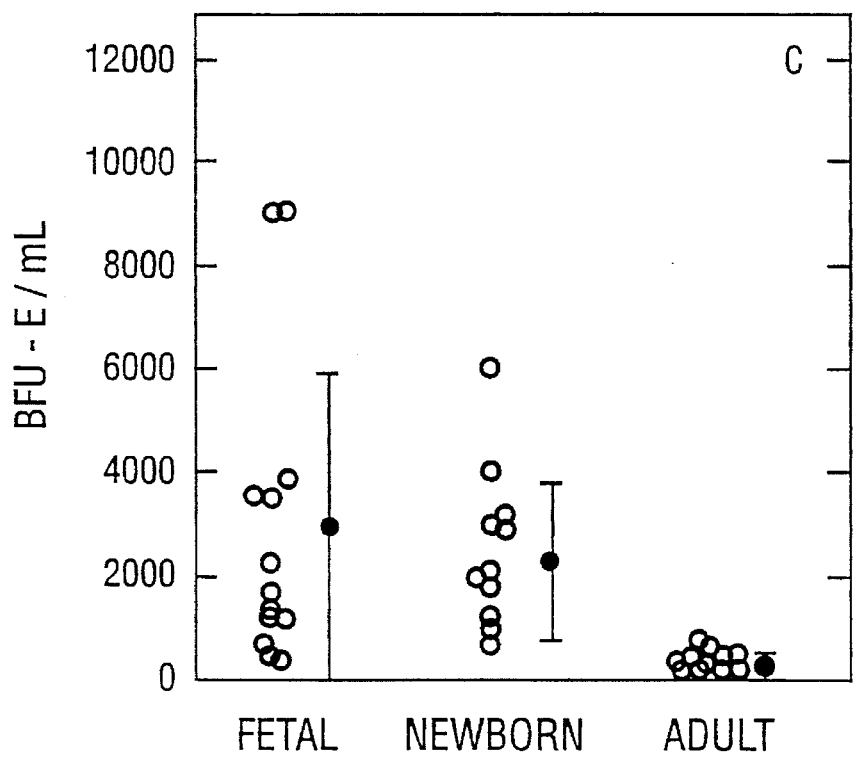
Figure 4B:
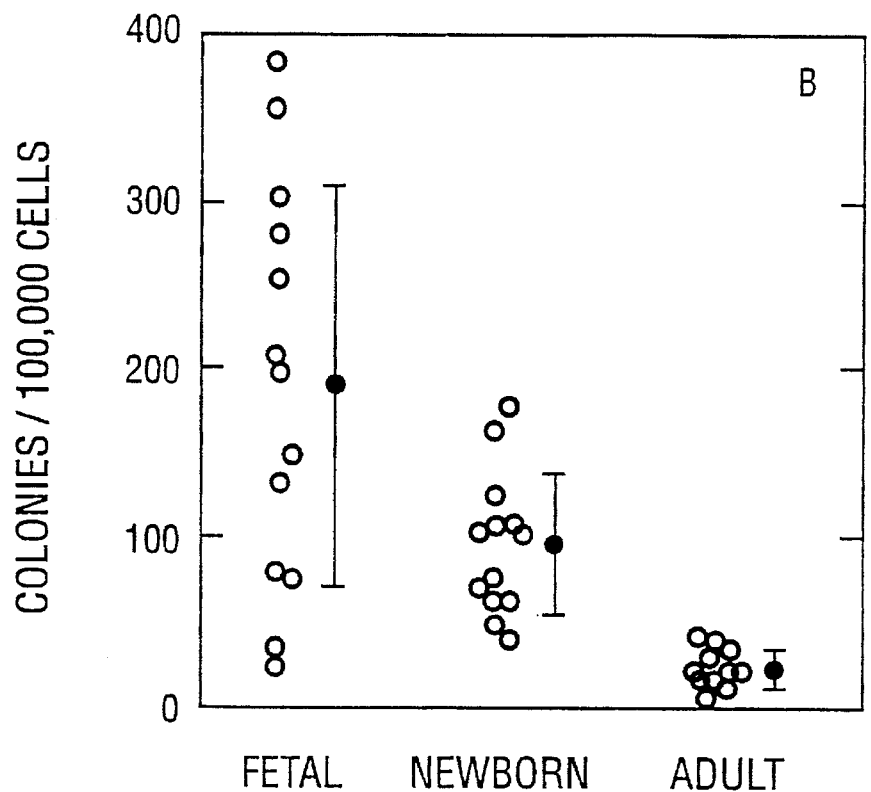
Figure 4D:
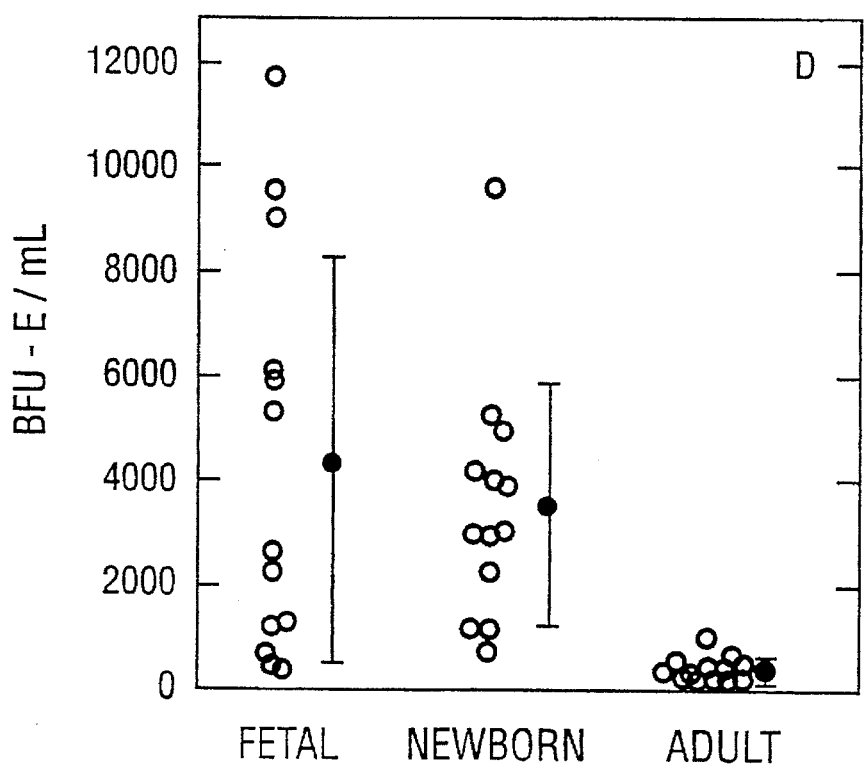
Figure 5A:
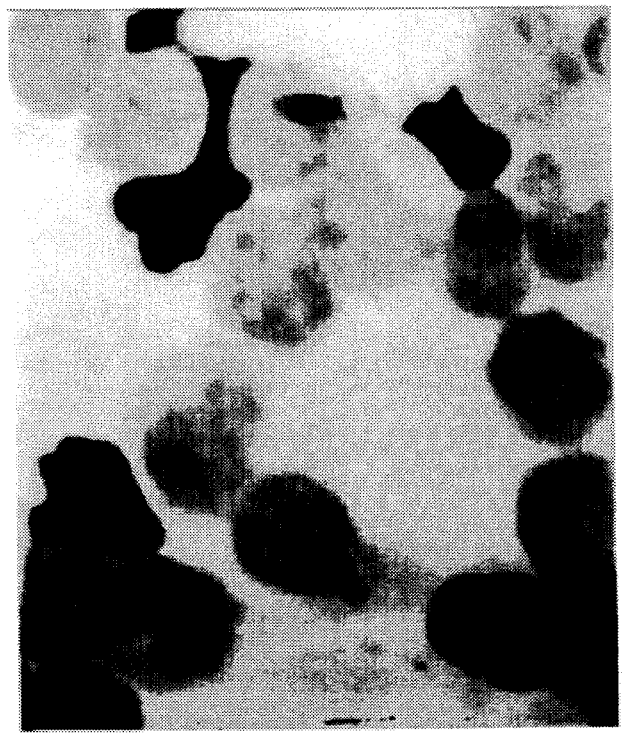
FIGS. 5A–5D shows morphology of erythroid differentiation in liquid cultures. All slides were stained with benzidine Wright-Giemsa, original magnification ×1,000.
Figure 5B:
Figure 5C:
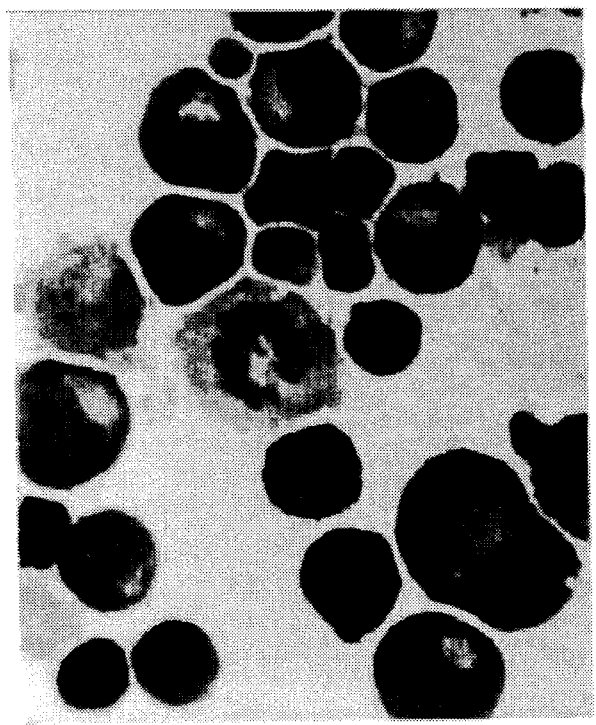
Figure 5D:
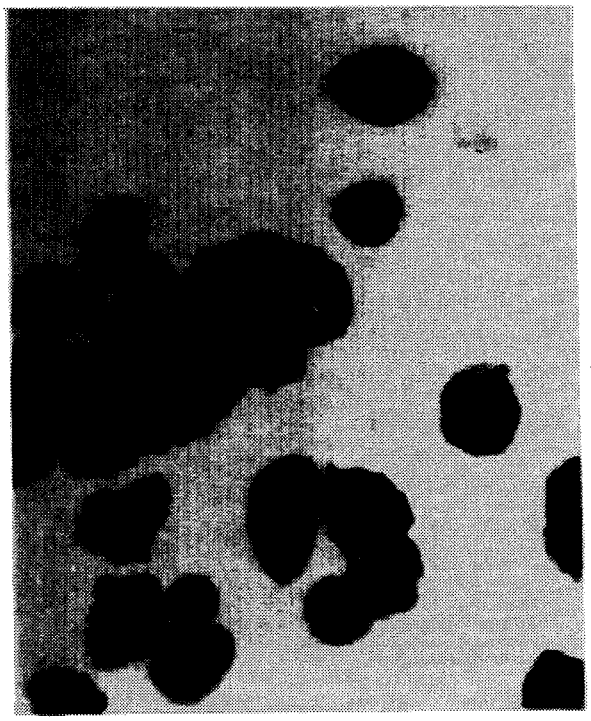

The present invention capitalizes on differences at the level of the erythroid progenitors (Weinberg et al. 1992; Forestier et al.) and stimulation sensitivities. One parameter was defined by Ep dose response curves (FIG. 3). Ep is required for growth of fetal or adult BFU-E. Fetal BFU-E are more sensitive to Ep than are adult BFU-E, with the Ep ½ max (the Ep required for 50% of maximal growth) 0.3 compared to 0.4 U/mL (Table 2).

TABLE 2

| | Erythropoiesis During Ontogeny | | |
|---|---|---|---|
| Parameter | Fetal | Newborn | Adult |
| BFU-E/100,000 MNC | 190 ± 120 | 95 ± 42 | 21 ± 11 |
| BFU-E/mL | 4300 ± 3900 | 3500 ± 2300 | 370 ± 230 |
| Ep half-max | 0.3 ± 0.2 | 0.4 ± 0.3 | 0.4 ± 0.3 |
| Hb F synthesis % | 82 ± 5 | 44 ± 12 | 13 ± 9 |

MNC = mononuclear cells. Data are mean ± 1 SD.

The more compelling observation is that 20–40% of the fetal colonies appeared at an Ep concentration of 0.01 U/mL, while <5% of the adult colonies grew at that low Ep concentration. Most fetal cultures reached maximal growth at Ep <2 U/mL, while most adult cultures required ≧2 U/mL. Thus the choice of Ep concentration used for the cultures may be important for selective enrichment of fetal erythroid progeny.

Colonies derived from fetal BFU-E are larger than those from adult BFU-E, with more subcolonies and more total cells. Under standard culture conditions (Ep 2 U/mL, 14 days), there are on average 10-fold more BFU-E in fetal blood, expressed as either BFU-E per $10^5$ mononuclear cells plated, or particularly per mL of blood (since the MNC/mL of blood is higher in fetal than adult blood) (Table 2 and FIG. 4). Since the fetal colonies are also larger, the overall relative amplification would be substantially more than 10-fold. The majority of the adult cultures took more than 14 days to achieve maximal growth, while the majority of the fetal cultures had reached their plateau by then. Thus it would appear that culture of MNC from the maternal circulation may lead to relative enrichment for fetal compared to adult progeny. Another obvious distinction between fetal and adult progenitors is that the erythroblasts in the fetal colonies synthesize predominantly fetal hemoglobin; this has potential application for prenatal diagnosis of hemoglobinopathies, as well as for identification of the fetal progeny.

The present invention also concerns additional distinctions between BFU-E at various stages of ontogeny. To this end a liquid culture system first described by Fibach et al. was modified (Weinberg et al. 1993). Mononuclear cells are cultured in phase 1 for about 7 days in the presence of stem cell factor (SCF), a recently described cytokine which acts at early as well as subsequent stages of erythropoiesis (McNiece et al.). The resulting nucleated cells are then recultured in phase 2 with Ep alone or also with SCF, for an additional 7 to 14 days (a total of 14 to 21 days). FIG. 5 shows day 0 mononuclear cells, day 7 cells, and the final products on day 14 and 21 from an adult blood culture. The initial and day 7 cells are primarily lymphocytes and monocytes, while the end result contains nucleated and anucleate erythroid cells. Cultures from newborns are compared with those from adult blood. The maximum final amplification of newborn cells was 8 to 45-fold, of which 50–100% were erythroid (Table 3).

TABLE 3

| | Liquid Cultures | | | |
|---|---|---|---|---|
| Phase 2 Additive | Newborn Fold Amplify | Newborn Erythroid % | Adult Fold Amplify | Adult Erythroid |
| Ep | 3.1–5.6 | 50–100 | 1.6–3.2 | 20–60 |
| Ep + SCF | 7.5–45 | 50–100 | 2.6–5.3 | 60–90 |

In the adult cultures, amplification was 3 to 5-fold, containing 60–90% erythroid cells. There was an approximately 10-fold relative advantage of newborn over adult cells in this system, compared with 5 to 10-fold for newborn and 10-fold for fetal in the methyl cellulose assay (Table 3).

Multiple sources of cord and adult cells were cultured in liquid media with and without SCF or the combination of SCF, IL3 and IL6 (See results in Table 4). 20–40 ml of blood was collected from normal adults or umbilical cords following delivery of normal infants, and placed into vacutainer tubes containing Na heparin. It was kept at room temperature and processed within one hour. The blood was diluted 1:1 with alpha medium (GIBCO) and layered into Ficoll-hypaque (Pharmacia) at a ratio of 20–25 ml of diluted blood per 20 ml of Ficoll. Mononuclear cells (MNC) were isolated by centrifugation on Ficoll-hypaque at 18°C. for 30 min at 450 xg. The plasma and medium were removed, and the interface layer containing the MNC was collected into 20 ml of alpha medium containing 2% fetal calf serum (FCS). The cells were washed twice with the same conditions, and resuspended in alpha medium with 2% FCS. The MNC were then cultured at $5 \times 10^6$ /ml for 7 days in alpha medium (with penicillin 0.1 u/ml and streptomycin 0.1 µg/l) with 10% FCS alone, or + SCF 100 ng/ml, or + SCF (AMGEN) 100 ng/ml+IL-3 (Immunex) 100 ng/ml+IL-6 (Genetics Institute) 100 u/ml. The room air incubator had high humidity and 5% $CO_2$. The nonadherent cells were then recovered by aspirating the medium containing the cells after a gentle shake of the flask, and centrifugation as above. The cells were replated at $3 \times 10^5$/ml in alpha medium with 30% FCS, 1% bovine serum albumin (BSA), $10^{-4}$M β-mercaptoethanol, penicillin 0.1 u/ml and streptomycin 0.1 µg/ml, as well as SCF 100 ng/ml, IL-3 100 ng/ml, and IL-6 100 u/ml. Incubations were in humidified incubators with 5% $CO_2$, and either room air or 5% oxygen. After 21 days, the cells were recovered by shaking the flasks and aspiration of medium containing cells. Cells were counted in a Coulter ZBI, and cytocentrifuge slides made and stained with benzidine-Wright's-Giemsa.

TABLE 4

Liquid Culture: Amplification of Cord Compared to Adult Cells

|  | CORD | | | ADULT | | |
|---|---|---|---|---|---|---|
|  | FCS | SCF | S36 | FCS | SCF | S36 |
|  | 60 | 59 | 50 | 1.6 | 0.8 | 2.4 |
|  | 41 | 62 | 13 | 1.3 | 1 | 0.5 |
|  | 46 | 42 | 52 | 1.6 | 0.7 | 0.9 |
|  | 19 | 70 |  | 2.1 | 1.8 |  |
|  | 15 | 20 |  |  |  |  |
|  | 49 | 17 |  |  |  |  |
|  |  | 63 |  |  |  |  |
| Number | 6 | 7 | 3 | 4 | 4 | 3 |
| Mean ± SD | 39 ± 16 | 48 ± 20 | 38 ± 18 | 1.7 ± 0.3 | 1.1 ± 0.5 | 1.3 ± 0.8 |

FCS = fetal calf serum with no added cytokines. SCF = stem cell factor. S36 = SCF, IL-3 and IL-6. These reagents were added in Phase 1 (day 0 to 7). Phase 2 (day 7 to 21) had erythropoietin, SCF, IL3, and IL6.

Figure 6:
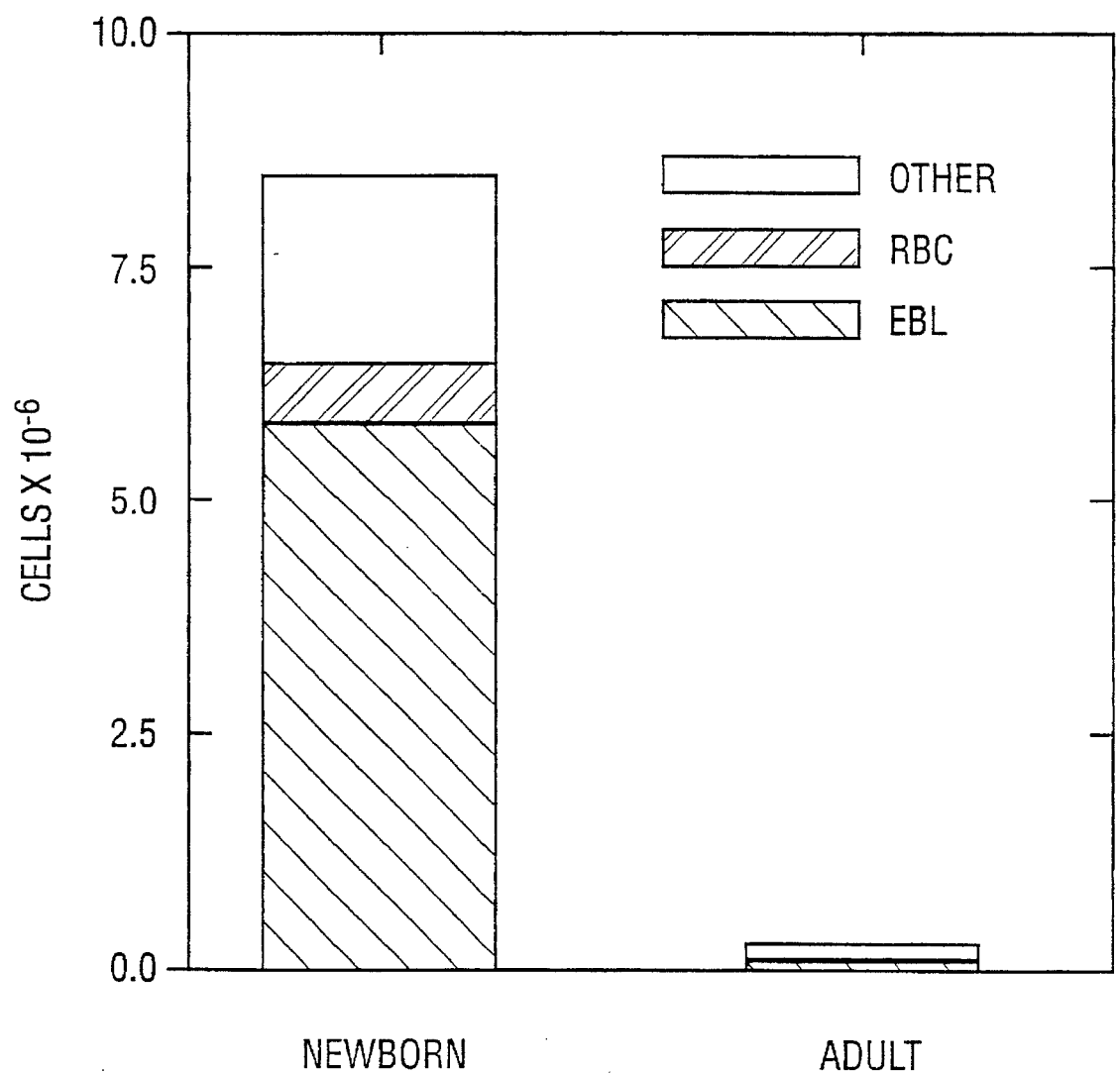
FIG. 6 shows numbers of cells recovered after plating 100,00 blood mononuclear cells in liquid culture. The first 7 days were without cytokines, while the second 14 days were with Ep, SCF, IL-3, and IL-6. Left, newborn. Right, adult. Solid bar, hemoglobinized (polychromatophilic and orthochromatic) erythroblasts. Hatched bar, erythrocytes. Open bar, other nucleated cells (leukocytes and non-hemoglobinized erythroblasts). Note the more than 80-fold amplification of cell numbers in the newborn culture, compared with less than 2-fold in the adult experiment.

The liquid culture assay is being further optimized. Using the combination of cytokines (Ep, SCF, IL-3, IL-6) results in a more than 80-fold amplification of newborn and less than 2-fold of adult cells, with >50% of the cells in the erythroid series (FIG. 6). Thus the relative enrichment of newborn over adult cells is >40-fold; an even better growth should be obtained from fetal progenitors. The conditions were as described for Table 4.

The potential uses of methyl cellulose or liquid cultures are shown in Table 5. Culture and other conditions were as described for Table 4.

TABLE 5

Predictive Comparison of Methyl Cellulose and Liquid Erythroid cultures: Speculation

| Parameter | Methyl Cellulose | Liquid |
|---|---|---|
| Maternal blood, mL | 50 | 50 |
| Total MNC | $5 \times 10^7$ | $5 \times 10^7$ |
| Fetal MNC 1/50,000 | 1,000 | 1,000 |
| Plating Phase 1, MNC/mL of culture | $3 \times 10^5$ | $5 \times 10^6$ |
| Volume of culture, mL | 150 | 10 |
| Plating Phase 2, MNC/mL of culture |  | $3 \times 10^5$ |
| Volume of culture, mL |  | 150 |
| Total BFU-E 20/$10^5$ | 1,000 |  |
| Fetal BFU-E 200/$10^5$ | 2 |  |
| Total cells (1,000/burst) | $10^7$ | $2 \times 10^8$ |
| Fetal cells | 2,000 | 100,000 |
| Days | 16 | 21 |
| Fetal/maternal | 1/5,000 | 1/2,000 |

MNC = mononuclear cells.

Fifty mL of maternal blood normally yields at least $5 \times 10^7$ mononuclear cells. Assuming one fetal cell per 50,000 maternal cells (which is based on the estimates outlined above from examination of erythrocytes or lymphocytes) there would be 1,000 fetal mononuclear cells. Assuming 20 adult BFU-E per $10^5$ adult MNC, and 200 fetal BFU-E per $10^5$ fetal MNC, there would be 10,000 adult bursts and 2 fetal bursts. When a burst has an average of 1,000 cells (although fetal bursts have more) there are more than 2,000 fetal cells and $10^7$ adult cells in methyl cellulose cultures, or 1/5,000. The liquid culture system is more useful, however. Numbers described here are minimal figures. Five$\times 10^7$ adult MNC are amplified a maximum of 4-fold, yielding $2 \times 10^8$ adult cells, while the 1,000 fetal MNC therein are amplified at least 100-fold, yielding $10^5$ fetal cells. The ratio of fetal to adult is now at least 1/2,000, from a starting material which had 1/50,000 fetal/adult cells. From the same volume of maternal blood, the liquid system thus provides a larger number of fetal cells.

Several types of manipulations may be used before or after the cells are cultured, based on the markers shown in Table 1. Stem and/or progenitor cells could be enriched using CD34, CD33, 17F11, DR, or CD71. The separation method could be panning, magnetic beads, MACS, or FACS. The enrichment could be done on day 0, or at some time during the initial phase of culture. During the next, Ep-dependent phase, cells may be recovered and enriched for the erythroid lineage using CD71, CD36, blood group antigens, or GPA. Although none of these separation maneuvers necessarily changes the ratio of fetal/maternal cells, they increase the total yield of erythroid cells. Selective enrichment for cells of fetal origin can be accomplished with the appropriate paternal blood group antigens, or with antibodies to fetal erythrocyte features, such as fetal hemoglobin or i antigen, a membrane antigen specific to fetal red cells.

The cultures can also be exploded using cytokine manipulations which favor fetal rather than adult growth. Such conditions include low concentration of Ep (Weinberg et al. 1992), addition of IL-6 (Gardner et al.), or a combination of factors including Ep, SCF, IL-3, and IL-6.

Prenatal diagnosis using fetal cells in the maternal circulation are performed as follows:

Blood (50 ml) is taken from a pregnant woman at 8–20 weeks gestation. MNC are isolated by centrifugation on Ficoll-hypaque, and cultured at $5 \times 10^6$/ml for 7 days in alpha medium with 10% FCS, using SCF 100 ng/ml, IL-3 100 ng/ml, and IL-6 100 u/ml. The nonadherent cells are then recovered and replated at $3 \times 10^5$/ml in alpha medium with 30% FCS, 1% BSA, $10^{-4}$M β-mercaptoethanol, and penicillin and streptomycin, as well as SCF 100 ng/ml, IL-3 100 ng/ml, and IL-6 100 µ/ml. All incubations are done in humidified incubators with 5% $CO_2$, and either room air or 5% oxygen. After 21 days, the cells are recovered.

(1) Cyto-centrifuge slides are made with $2 \times 10^5$ cells, and stained with fluorescent antibody to γ-globin (of fetal hemoglobin), followed by FISH analysis using probes for DNA sequences of interest. These would include X, Y, and chromosomes 13, 18, and 21. They could also include specific genes known to be mutant in the family, either deleted or amplified.

(2) Cells are centrifuged and DNA extracted using standard methods, for PCR amplification using probes specific for the mutant gene(s) for which the fetus is at risk.

(3) Cells are treated with vinblastine for 1 hour to arrest metaphases, and standard methods are used to prepare slides for cytogenetic analysis.

(4) RNA is extracted from the cells, and used for reverse transcription PCR of RNA for globin or other red cell specific proteins, such as spectrin or other membrane proteins, or red cell enzymes.

Only analysis (1) takes advantage of the unique marker for the fetal erythroid cells, anti-γ globin. This is a very powerful marker, however, because identification of fetal cells which are all normal may suffice to exclude the at-risk disease. Without specific identification of the fetal cells, failure to detect a mutation is always suspect.

Analysis (4) capitalizes on the growth of large quantities of erythroid cells.

Analysis (2) utilizes the relative amplification of fetal cells; PCR will be more reliable with fetal/adult ratios of abut 1/2000 compared to the about 1/50,000 prior to culture.

Analysis (3) still requires very labor-intensive methods, although an automated metaphase finder makes this analysis feasible; it would require observation of a few abnormal cells among many normal (i.e., 1/2000).

Alternatives are available for enhancing the above procedure to enrich for progenitor cells or stem cells, to reduce the number of cells to place in culture in the first phase. This may be accomplished by negative selection (removal of monocytes and T cells), as well as positive selection using e.g., CD34.

On about day 7, cells that have characteristics of early erythroid cells may be enriched (e.g., CD71).

On about day 14 or 21 erythroid cells may be enriched, e.g., using CD71, CD36, and/or GPA.

The cells which result from these cultures are not purely fetal, but are relatively more so than the starting material and may be subjected to the same analytical techniques that have been used for unseparated material, mainly PCR, FISH, or karyotyping. In addition, globin mRNA could be recovered and used for RT-PCR for the diagnosis of hemoglobinopathies. The erythroid cells which are of fetal origin can be identified by staining with fluorescent antibodies to fetal hemoglobin.

The following references are incorporated in pertinent part by reference herein for the reasons cited in the above text.

Alter, B. P., 1991, "Bone marrow failure disorders," Mt. Sinai J. Med., 58:521–34.

Axelrad, et al., 1973, "Properties of cells that produce erythrocytic colonies in vitro," In HEMOPOIESIS IN CULTURE, W. A. Robinson, Ed., DHEW Publication No. (NIH) 74–205, pp. 226–34.

Bianchi et al. 1990, "Isolation of fetal DNA from nucleated erythrocytes in maternal blood," Proc. Natl Acad Sci. USA, 87:3279–83.

Bianchi et al., 1993, "Erythroid-specific antibodies enhance detection of fetal nucleated erythrocytes in maternal blood," Prenat Diagn. 13:293–300.

Bruch et al., 1991, "Trophoblast-like cells sorted from peripheral maternal blood using flow cytometry: a multiparametric study involving transmission electron microscopy and fetal DNA amplification," prenat. Diagn., 11:787–98.

Cacheux, et al., 1992, "Detection of 47,XYY trophoblast fetal cells in maternal blood by fluorescence in situ hybridization after using immunomagnetic lymphocyte depletion and flow cytometry sorting, Fetal Diagn. Ther., 7:190–94

Covone et al., 1984, "Trophoblast cells in peripheral blood from pregnant women," Lancet. 2:841–43.

Covone et al., 1988, "Analysis of peripheral maternal blood samples for the presence of placenta-derived cells using Y-specific probes and McAb H315," Prenat. Diagn., 8:591–607.

De Grouchy et al., 1971, "Transfusion foeto-maternelle de lymphocytes sanguins et détection du sexe du foetus,"Ann. Génét. 14:133–37.

Fibach et al., 1989, "Proliferation and maturation of human erythroid progenitors in liquid culture," Blood, 73:100–03.

Forestier, et al, 1991, "Developmental hematopoiesis in normal human fetal blood," Blood, 77:2360–63.

Gänshirt-Ahlert et al., 1992, "Magnetic cell sorting and the transferrin receptor as potential means of prenatal diagnosis from maternal blood," Am. J. Obstetr. Gynecol., 155:1350–55.

Gardner et al., 1990, "Effects of interleukin-6 on fetal hematopoietic progenitors," Blood 75:2150–55.

Grosset et al., 1974, "Antenatal fetal sex determination from maternal blood during early pregnancy," Am. J. Obstetr. Gynecol., 120:60–63.

Hamada et al., 1993, "Fetal nucleated cells in maternal peripheral blood: frequency and relationship to gestational age," Hum. Genet. 91:427–32.

Herzenberg et al., 1979, "Fetal cells in the blood of pregnant women: Detection and enrichment by fluorescence-activated cell sorting," Proc. Natl Acad. Sci. USA. 76:1453–55.

Iverson et al., 1981, "Detection and isolation of fetal cells from maternal blood using the fluorescence-activated cell sorter (FACS)" Prenat. Diag., 1:61-73

Kao et al., 1992, Analysis of peripheral blood of pregnant women for the presence of fetal Y chromosome-specific ZFY gene deoxyribonucleic acid sequences," Am. J. Obstetr. Gynecol. 166:1013–19.

Kirsch-Voiders, et al., 1980, "Increase in the amount of fetal lymphocytes in maternal blood during pregnancy, J. Med. Genet., 17:267–72.

Kulozik et al., 1982, "Fetal cells in the maternal circulation: Detection by direct AFP-immunofluorescence,"Hum. Genet., 62:221-224.

Lo et al., 1993, "Prenatal sex determination from maternal peripheral blood using the polymerase chain reaction,"Hum. Genet. 90:483–88.

Loken et al., 1987, "Flow cytometric analysis of human bone marrow: I. Normal erythroid development," Blood, 69:255–63.

McNiece et al., 1991, "Recombinant human stem cell factor synergizes with GM-CSF, G-CSF, IL-3 and Epo to stimulate human progenitor cells of the myeloid and erythroid lineages," Exp. Hematol., 19:226–31.

Mueller et al, 1990, "Isolation of fetal trophoblast cells from peripheral blood of pregnant women," Lancet. 336197–200.

Nakagome et al., 1991, "Absence of fetal cells in maternal circulation at a level of 1 in 25,000," Am. J. Med. Genet., 40:506–508.

Okumura et al., 1992, "Changes in cell surface antigen expressions during proliferation and differentiation of human erythroid progenitors,' Blood 80: 642–50.

Papayannopoulou et al., 1991, "Isolation of c-kit receptorexpressing cells from bone marrow, peripheral blood, and fetal liver: Functional properties and composite antigenic profile," Blood 78: 1403–12.

Parks et al., 1982, "Fetal cells from maternal blood: Their selection and prospects for use in prenatal diagnosis,"Methods in Cell Biology, 26:277–95.

Pool et al., 1987, "Trophoblast cells and maternal blood," Lancet., i: 804–05.

Price et al. "Prenatal diagnosis with fetal cells isolated from maternal blood by multiparameter flow cytometry, "Am. J. Obstetr. Gynecol., 165:1731–37.

Schroder, J., 1975, "Transplacental passage of blood cells,"J. Med. Genet. 12:230–42.

Schröder et al., 1972, "Fetal lymphocytes in the maternal blood," Blood 39:153–162.

Siebers et al., 1975, "Antenatal sex determination in blood from pregnant women," Humangenetik, 28:273–280.

Sieff et al., 1982, "Changes in cell surface antigen expression during hemopoietic differentiation, Blood, 0:703–713.

Walknowska, et al. "Practical and theoretical implications of fetal/maternal lymphocyte transfer," Lancet, 1:1119–1122.

Weinberg et al., 1983, "Switch from fetal to adult hemoglobin is associated with a change in progenitor cell population," J. Clin. Invest., 71:785–94.

Weinberg et al., 1992, "Erythropoiesis is distinct at each stage of ontogeny," Pediatr. Res., 31:170–75.

Weinberg et al., 1993, "Stem cell factor amplifies newborn and sickle erythropoiesis in liquid cultures," Blood, 1:2591–99.

Wessman et al., 1992, "Fetal granulocytes in maternal venous blood detected by in situ hybridization," prenat. Diagn. 12:993–1000.

Zipursky et al., 1959, "Foetal erythrocytes in the maternal circulation," Lancet 1:451–52.

It is understood that equivalent variations in procedures and stimulatory agents of the following claims are known to those of skill in the art to accomplish the selective amplifications and analyses, once the knowledge described herein is studied.

What is claimed is:

1. A process for obtaining a cell sample enriched in fetal cells from maternal blood consisting essentially of;

obtaining cells from a maternal blood sample;

selectively stimulating fetal cell growth by incubating said cells in a medium comprising a composition of cytokines consisting essentially of erythropoietin, stem cell factor, interleukin-3 and interleukin-6 to produce a cell sample enriched in fetal cells.

2. A process for prenatal genetic analysis consisting essentially of:

obtaining cells from a maternal blood sample;

selectively stimulating fetal cell growth by incubating said cells in a medium comprising a composition of cytokines consisting essentially of erythropoietin, stem cell factor. interleukin-3 and interleukin-6 to produce a cell sample enriched in fetal cells; and analyzing fetal cells for genetic content or abnormalities.

3. The process of claim 1 or 2, wherein the selectively stimulatory step is defined further as comprising initially incubating said cells in a medium consisting essentially of stem cell factor.

4. The process of claim 1 or 2 where each of stem cell factor, interleukin-3 and interleukin-6 is at an amount of up to 100 ng/ml and erythropoietin is in an amount of up to 2 U/ml.

5. The process of claim 1 or 2 where fetal cell concentration is monitored by using an antibody specific for a fetal cell antigen.

6. The process of claim 5 where the fetal cell antigen is fetal hemoglobin or i antigen.

7. The process of claim 1 or 2 where the fetal cells are fetal hematopoetic progenitor cells.

* * * * *